(12) United States Patent
Nguyen

(10) Patent No.: US 11,300,252 B2
(45) Date of Patent: Apr. 12, 2022

(54) ILLUMINATION DEVICES

(71) Applicant: Ronald C. Nguyen, Fountain Valley, CA (US)

(72) Inventor: Ronald C. Nguyen, Fountain Valley, CA (US)

( * ) Notice: Subject to any disclaimer, the term of this patent is extended or adjusted under 35 U.S.C. 154(b) by 0 days.

(21) Appl. No.: 16/677,617

(22) Filed: Nov. 7, 2019

(65) Prior Publication Data
US 2021/0140593 A1 May 13, 2021

(51) Int. Cl.
| | |
|---|---|
| *F21L 4/06* | (2006.01) |
| *G02C 11/04* | (2006.01) |
| *F21V 23/00* | (2015.01) |
| *F21V 23/06* | (2006.01) |
| *A61B 90/35* | (2016.01) |
| *F21V 23/04* | (2006.01) |

(52) U.S. Cl.
CPC .............. *F21L 4/06* (2013.01); *F21V 23/001* (2013.01); *F21V 23/06* (2013.01); *G02C 11/04* (2013.01); *A61B 90/35* (2016.02); *F21V 23/0414* (2013.01)

(58) Field of Classification Search
CPC .......... F21L 4/06; G02C 11/04; F21V 23/001; F21V 23/06; F21V 23/0414; A61B 90/35
See application file for complete search history.

(56) References Cited

U.S. PATENT DOCUMENTS

| | | | |
|---|---|---|---|
| 3,609,262 A | 9/1971 | Hotchkiss | |
| 4,872,093 A * | 10/1989 | Shimizu | G01D 11/28 362/23.15 |
| 5,268,826 A | 12/1993 | Greene | |
| 6,863,411 B2 * | 3/2005 | Furuya | G01D 13/28 362/23.18 |
| 7,008,074 B1 | 3/2006 | Halm | |
| 7,175,295 B2 * | 2/2007 | Bretz | F21L 2/00 362/108 |
| 7,500,747 B2 * | 3/2009 | Howell | G02C 11/06 351/158 |
| 8,094,858 B2 * | 1/2012 | Thiel | G02C 3/003 381/381 |
| 8,261,686 B2 * | 9/2012 | Birman | B60K 37/02 116/286 |
| 8,653,702 B2 | 2/2014 | Saleh | |
| 9,362,664 B2 | 6/2016 | Yen | |

(Continued)

*Primary Examiner* — Tsion Tumebo
(74) *Attorney, Agent, or Firm* — Jinn Su

(57) ABSTRACT

Illumination devices are described. Illumination devices may be for use with eyewear capable of being worn on a face of a user. In one embodiment, an illumination device may comprise a battery assembly having a battery housing and a battery connector. The battery assembly may be configured to be worn by the user. The illumination device may also comprise a light assembly having a light source coupled by a wire to a light connector. The light connector may be capable of being electrically coupled to the battery connector. The light assembly may be configured to be coupled to the eyewear. The illumination device may also comprise a hinge coupling hingedly coupling the light connector to the battery connector. The hinge coupling may have a closed configuration in which the light connector is electrically coupled to the battery connector. The hinge coupling may have an open configuration in which the light connector is not electrically coupled to the battery connector.

18 Claims, 23 Drawing Sheets

(56) References Cited

U.S. PATENT DOCUMENTS

| | | | |
|---|---|---|---|
| 9,568,343 B2* | 2/2017 | Birman | B60K 37/02 |
| 9,885,465 B2 | 2/2018 | Nguyen | |
| 10,066,816 B2 | 9/2018 | Chang | |
| 10,724,716 B2* | 7/2020 | Neeley | F21V 21/084 |
| 2006/0023158 A1* | 2/2006 | Howell | G02C 11/06 |
| | | | 351/41 |
| 2006/0067168 A1* | 3/2006 | Winkler | G04G 9/0041 |
| | | | 368/67 |
| 2006/0185576 A1* | 8/2006 | Tane | B60K 37/02 |
| | | | 116/288 |
| 2008/0002386 A1* | 1/2008 | Mezouari | G01D 11/28 |
| | | | 362/23.16 |
| 2008/0310145 A1* | 12/2008 | Blake | F21V 21/084 |
| | | | 362/105 |
| 2009/0109801 A1* | 4/2009 | Winkler | G04B 45/0015 |
| | | | 368/67 |
| 2012/0155064 A1* | 6/2012 | Waters | G02C 11/04 |
| | | | 362/103 |
| 2013/0235332 A1* | 9/2013 | Blum | F16M 11/04 |
| | | | 351/158 |
| 2014/0362561 A1* | 12/2014 | Faircloth | G02C 11/04 |
| | | | 362/103 |
| 2015/0226985 A1* | 8/2015 | Jones | G02C 3/006 |
| | | | 351/121 |
| 2016/0327246 A1* | 11/2016 | Nguyen | F21V 21/084 |
| 2018/0074341 A1* | 3/2018 | Loo | G02C 5/146 |
| 2019/0105784 A1 | 4/2019 | Hodges et al. | |
| 2019/0178477 A1 | 6/2019 | Ross | |

* cited by examiner

ILLUMINATION DEVICES

BACKGROUND

Illumination devices may be used to illuminate an area of interest. Illumination devices may be coupled to eyewear such as surgical loupes and dental loupes. Illumination devices may be turned on and off with light controls.

When an illumination device is worn on the face of the user, the user may need to operate the controls to turn on the illumination device. When the illumination device is removed from the face of a user, the illumination device may remain on, and the user may need to remember and then operate the controls to turn off the illumination device. This may be inconvenient, especially if the eyewear is frequently worn on and removed from the face of the user.

What is needed is an illumination device which automatically turns on when the eyewear is worn on the face of a user. What is needed is an illumination device which automatically turns off when the eyewear is removed from the face of a user.

Illumination devices may be turned on and off with controls that are touched with the hands. This may not be hygienic if the hands are not clean.

What is needed is an illumination device that may be turned on and off without being touched by the hands.

SUMMARY

Illumination devices are described. Illumination devices may be for use with eyewear capable of being worn on a face of a user. In one embodiment, an illumination device may comprise a battery assembly having a battery housing and a battery connector. The battery assembly may be configured to be worn by the user. The illumination device may also comprise a light assembly having a light source coupled by a wire to a light connector. The light connector may be capable of being electrically coupled to the battery connector. The light assembly may be configured to be coupled to the eyewear. The illumination device may also comprise a hinge coupling hingedly coupling the light connector to the battery connector. The hinge coupling may have a closed configuration in which the light connector is electrically coupled to the battery connector. The hinge coupling may have an open configuration in which the light connector is not electrically coupled to the battery connector.

BRIEF DESCRIPTION OF THE DRAWINGS

FIG. 1A shows illumination device 1000. FIG. 1B shows illumination device 1000, with battery assembly 1100 worn by a user and light assembly 1200 coupled to eyewear E.

FIGS. 6A-6B show a side view of the method. FIGS. 7A-7B show a rear view of the method.

DESCRIPTION

Figure 1A:
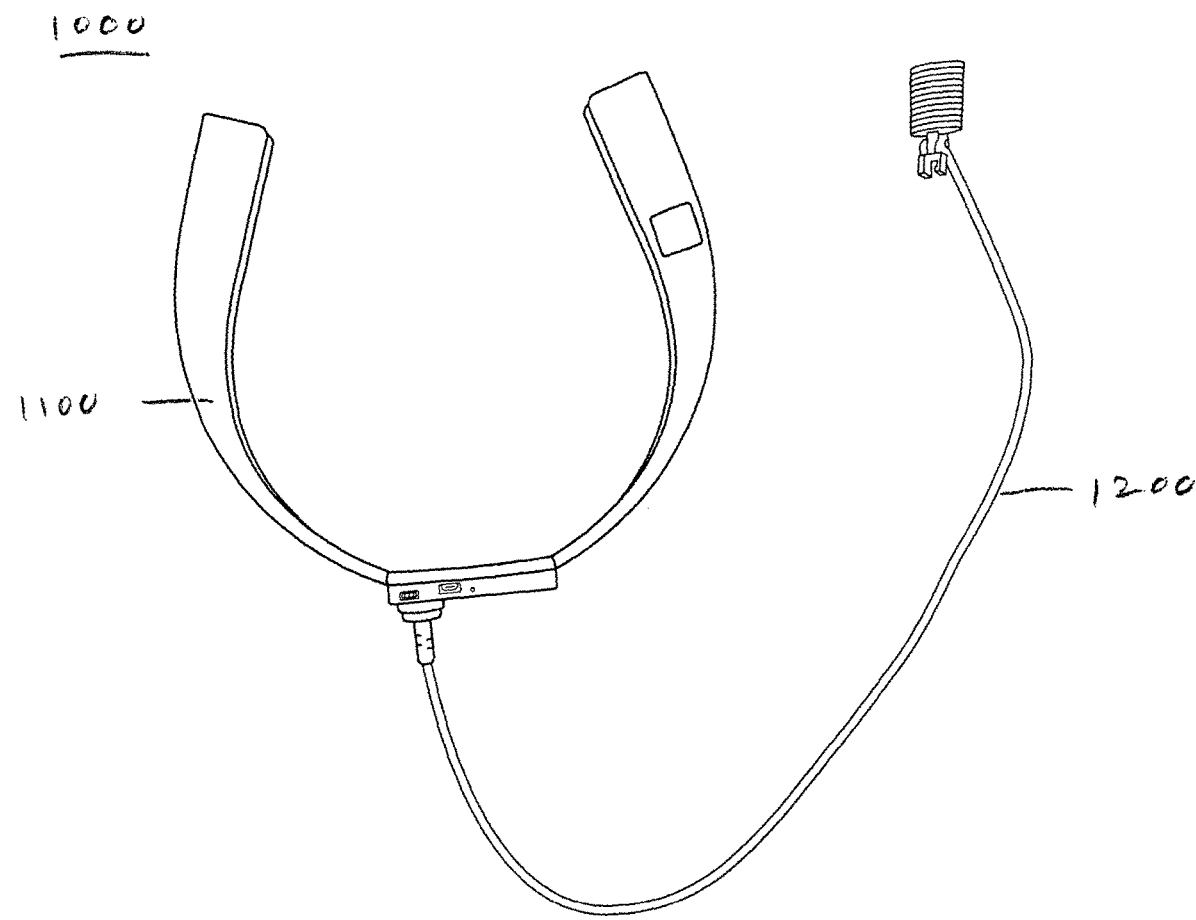
FIGS. 1A-1B show one embodiment of an illumination device 1000.
Figure 1B:
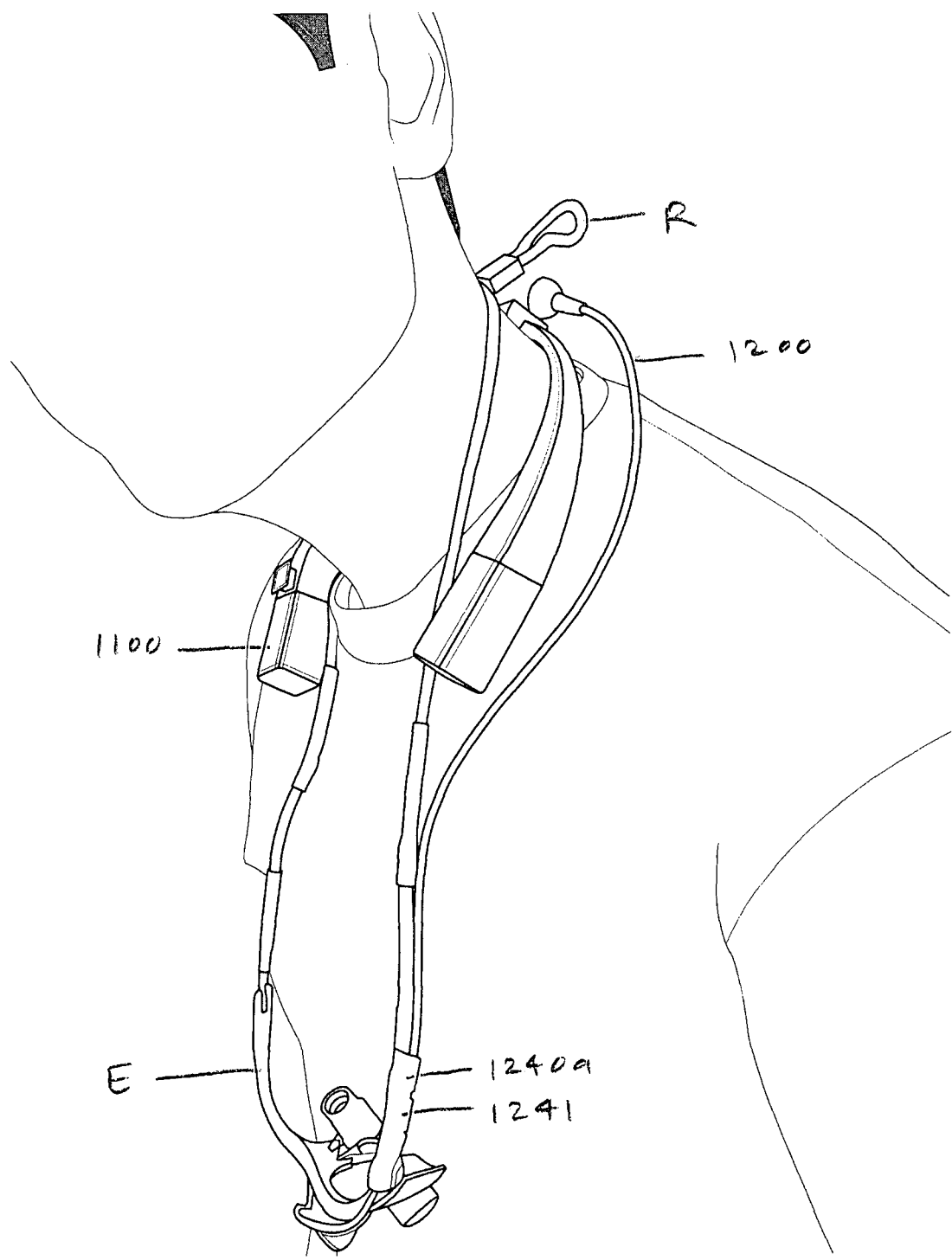

FIGS. 1A-1B show one embodiment of an illumination device 1000. FIG. 1A shows illumination device 1000. FIG. 1B shows illumination device 1000, with battery assembly 1100 worn by a user and light assembly 1200 coupled to eyewear E.

Illumination device 1000 may include a battery assembly 1100. Battery assembly 1100 may be configured to be worn by a user.

Figure 2A:
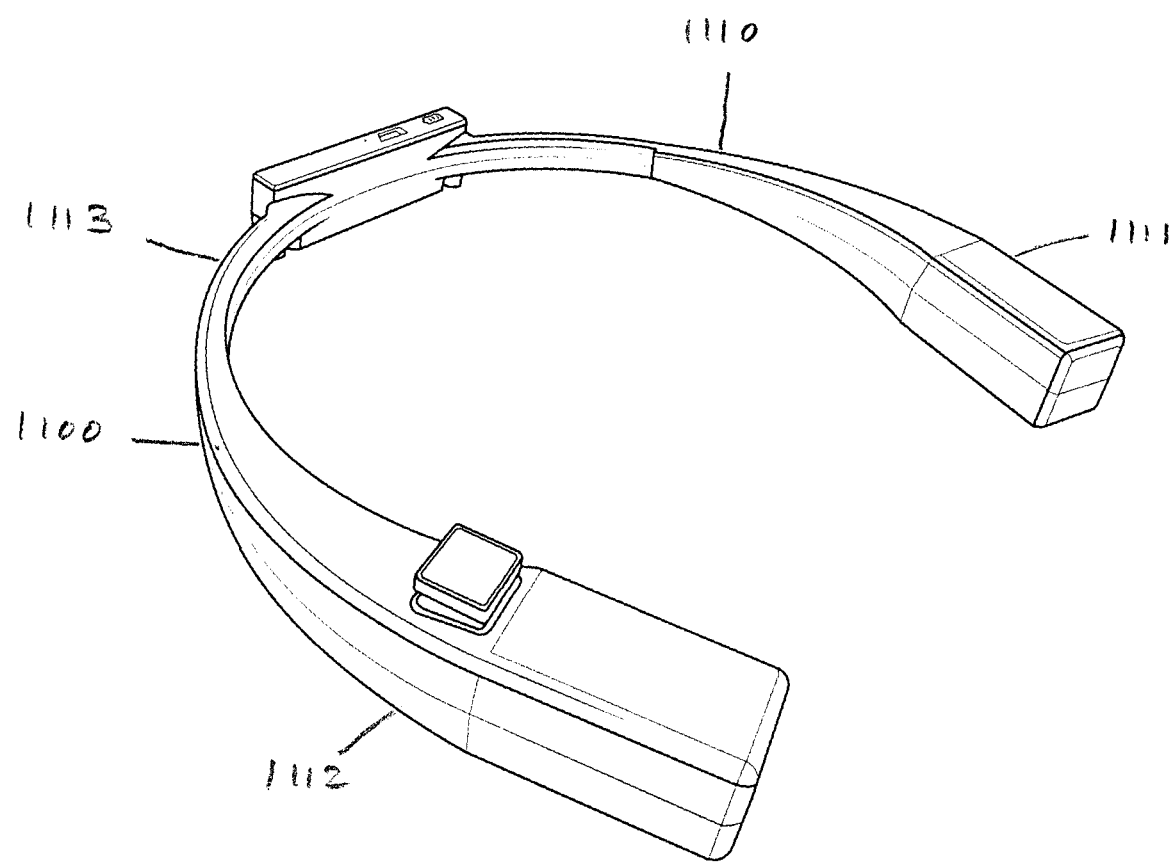
FIGS. 2A-2C show perspective, rear, and top views of one embodiment of a battery assembly 1100.
Figure 2B:
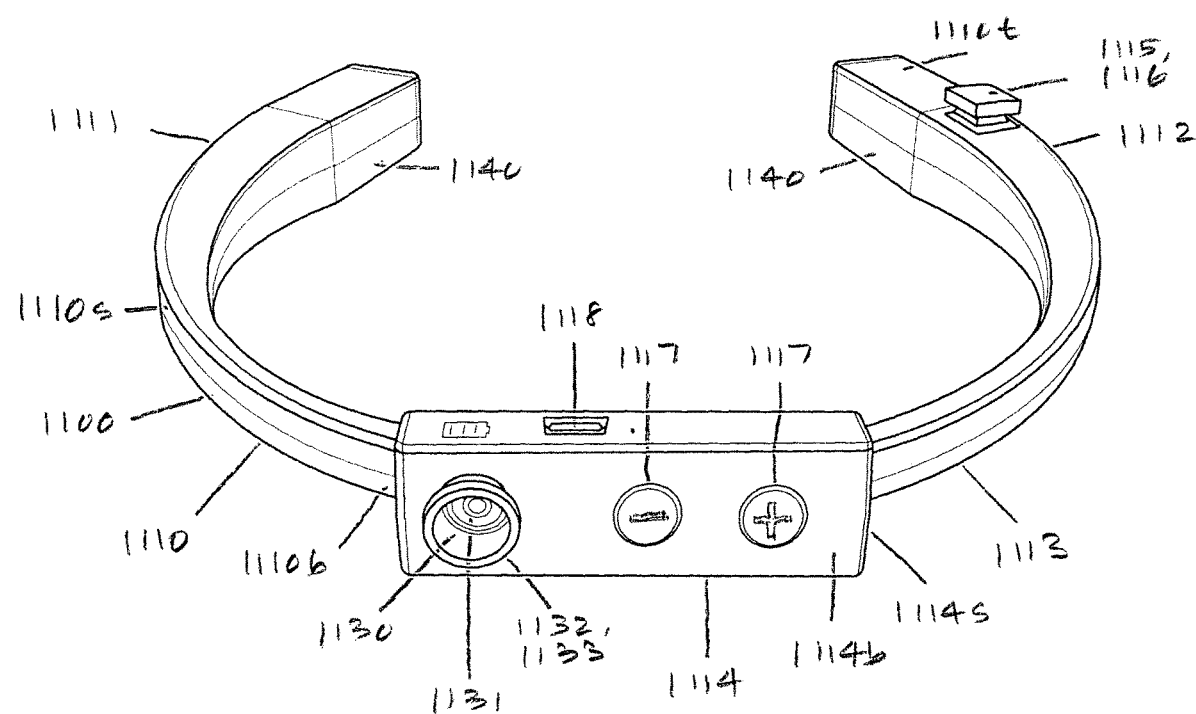
Figure 2C:
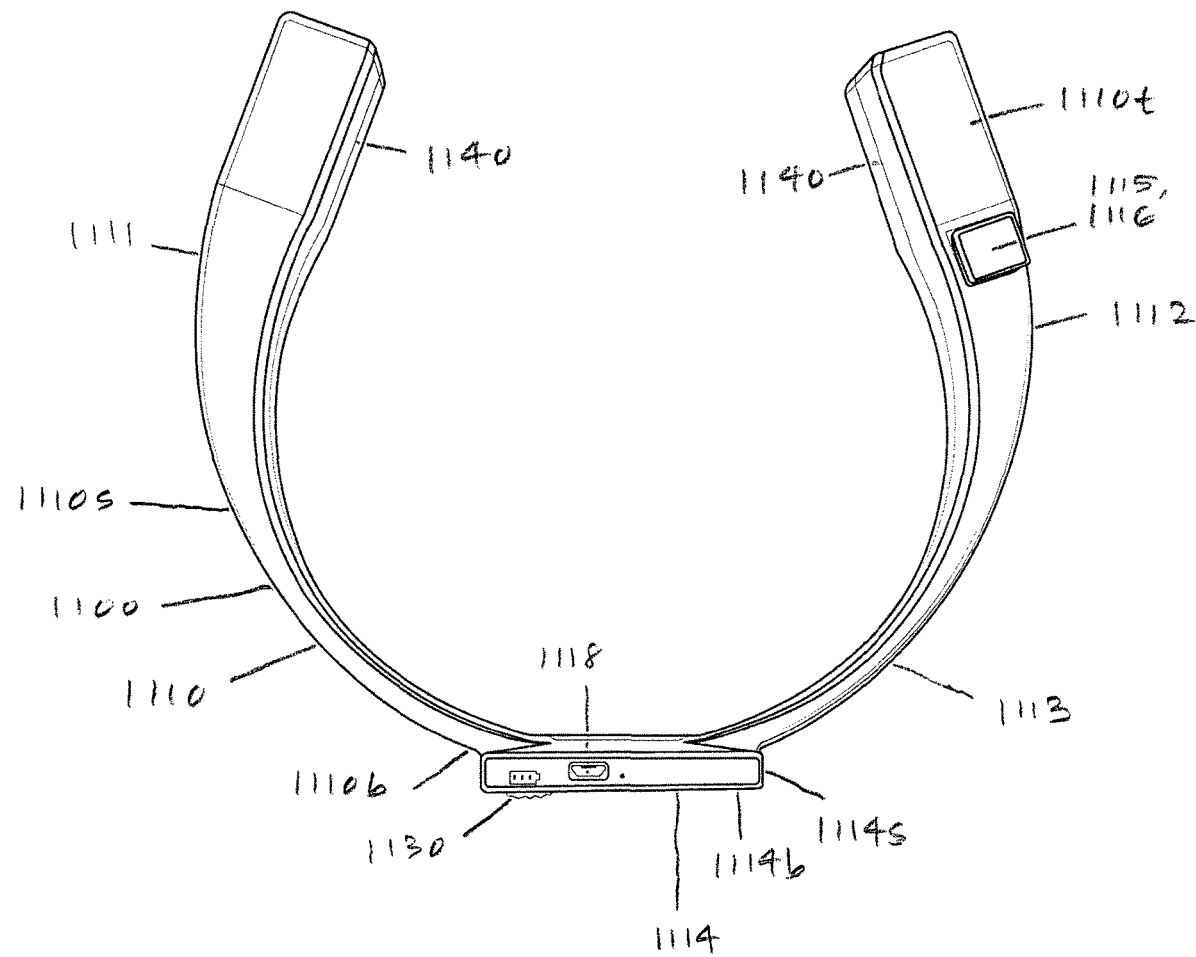
Figure 2D:
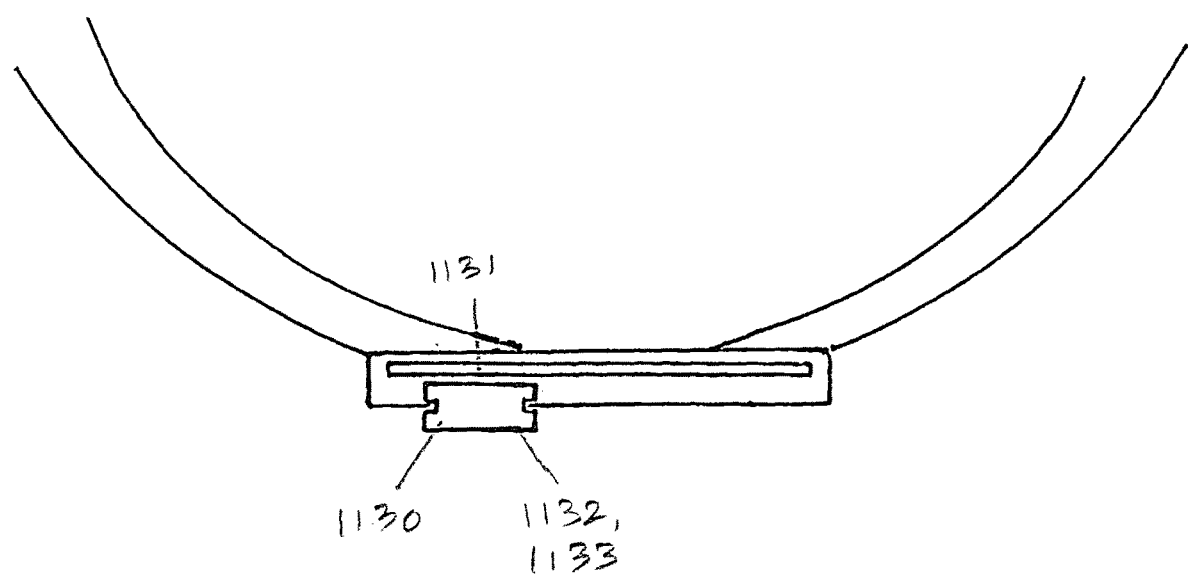
FIG. 2D shows a cross-sectional view of one embodiment of a battery connector 1130.

FIGS. 2A-2C show perspective, rear, and top views of one embodiment of a battery assembly 1100. FIG. 2D shows a cross-sectional view of one embodiment of a battery connector 1130.

Battery assembly 1100 may include a battery housing 1110. Battery housing 1110 may be configured to be worn by a user. Battery housing 1110 may be configured to be worn at least partially around the neck of a user.

Battery housing 1110 may be any suitable shape. At least a portion of the battery housing 1110 may be worn behind the neck of a user, or around the back of the neck of a user.

Battery housing 1110 may be U-shaped. Battery housing 1110 may include a left portion 1111 and a right portion 1112 coupled to a center portion 1113. Center portion 1113 may be configured to be worn behind the neck of a user, or around the back of the neck of a user. Center portion 1113 may have a width and/or cross-section that is smaller than left portion 1111 and/or right portion 1112. Left portion 1111 and right portion 1112 may be configured to extend forward along the sides of the neck of a user, or over the shoulders near the neck of a user. Left portion 1111 and right portion 1112 may be able to flex outward to fit around the neck of a user. Left portion 1111 and right portion 1112 may curve downward to fit closer to the upper chest of a user. Battery housing 1110 may have a cross-section that is one or more of rectangular, circular, oval, and any other suitable shape.

Battery housing 1110 may include a pod 1114. Pod 1114 may be coupled to center portion 1113 of battery housing 1110. Pod 1114 may be formed as part of or separate from battery housing 1110.

Battery assembly 1100 may include a light control 1115. Light control 1115 may be configured to be operated by a part of the face of a user. Light control 1115 may be configured to be operated by one or more of the chin, jaw, cheek, and mouth of a user.

Light control 1115 may be positioned to be operated by a part of the face of a user. Light control 1115 may be positioned within reach of a part of the face of a user. Light control 1115 may be coupled to an top surface 1110t of battery housing 1110, such as the top surface of left portion 1111 and/or the top surface of right portion 1112. Alternatively, or in addition, light control 1115 may be coupled to a bottom surface of battery housing 1110, such as the bottom surface of left portion 1111 and/or the bottom surface of right portion 1112, and operated by activating the switch between a part of the face of a user and the upper chest of a user.

Light control 1115 may include one or more of a button, capacitive sensor, IR sensor, or any other suitable device. Light control 1115 may include one or more devices.

Light control 1115 may be sized to be operated by a part of the face of a user. Light control 1115 may be sufficiently large to be operated by a part of the face of a user. Light control 1115 may have a diameter and/or width of approximately ⅛ inch to approximately 2 inch. Light control 1115 may protrude from a surface of battery housing 1110 to allow it to be operated by a part of the face of a user. Light control 1115 may protrude approximately 1/16 inch to approximately ¾ inch from a surface of battery housing 1110.

Light control 1115 may include a power switch 1116. Light control 1115 may include a brightness control. Light control 1115 may include a wavelength control.

Battery assembly 1100 may include a brightness control 1117. Brightness control 1117 may be coupled to pod 1114 or any other part of battery housing 1110. Brightness control 1117 may include one or more of a button, capacitive sensor, IR sensor, or any other suitable device. Brightness control 1117 may include one or more devices.

Battery assembly 1100 may include a recharging port 1118. Recharging port 1118 may be coupled to pod 1114 or any other part of battery housing 1110.

Battery assembly 1100 may include a battery connector 1130. Battery connector 1130 may be coupled to a portion of battery housing 1110 worn behind the neck of a user. Battery connector 1130 may be coupled to center portion 1113 of battery housing 1110. Battery connector 1130 may have a longitudinal axis 1130x.

Battery connector 1130 may include one or more battery contacts 1131. Battery contacts 1131 may include one or more of a pin, contact pad, and any other suitable contact. Battery contacts 1131 may include contact pads that are one or more of circular, ring-shaped, and any other suitable shape. Battery contacts 1131 may include one or more contact pads that are concentric.

Battery connector 1130 may include an alignment feature 1132. Alignment feature 1132 may protrude from a surface of battery housing 1110. Alignment feature 1132 may be circular, octagonal, hexagonal, square, or any other suitable shape.

Battery connector 1130 may include an attachment element 1133. Attachment element 1133 may be at least partially made of a magnetic material such as neodymium, a ferromagnetic material such as iron, or other suitable material. Attachment element 1133 may be shaped like a ring, or any other suitable shape. Attachment element 1133 may form at least a portion of alignment feature 1132.

Battery assembly 1100 may include one or more battery cells 1140. One or more battery cells 1140 may be coupled to left portion 1111 and/or right portion 1112. Battery cells 1140 may include one or more of lithium ion, nickel metal hydride, alkaline, and any other suitable power source.

Battery assembly 1100 may have sufficient weight to resist being moved by a light assembly 1200. Battery assembly 1100 may have a weight of approximately 0.5 ounces to approximately 12 ounces. Battery cells 1140 may weight battery housing 1110 forward when battery housing 1110 is worn by a user, and help to keep battery assembly 1100 in place when worn by a user.

Illumination device 1000 may include a light assembly 1200. Light assembly 1200 may be configured to be coupled to eyewear E. Light assembly 1200 may be coupled to the bridge, the temple, or any other suitable location of eyewear E. Eyewear E may be configured to be worn by a user. Eyewear E may include a surgical loupe, a dental loupe, safety glasses, or any other eyewear. Eyewear E may be used with an eyewear retainer R. Light assembly 1200 may be configured to be coupled to a mask, headwear, or any other article worn on the face or head.

Figure 3A:
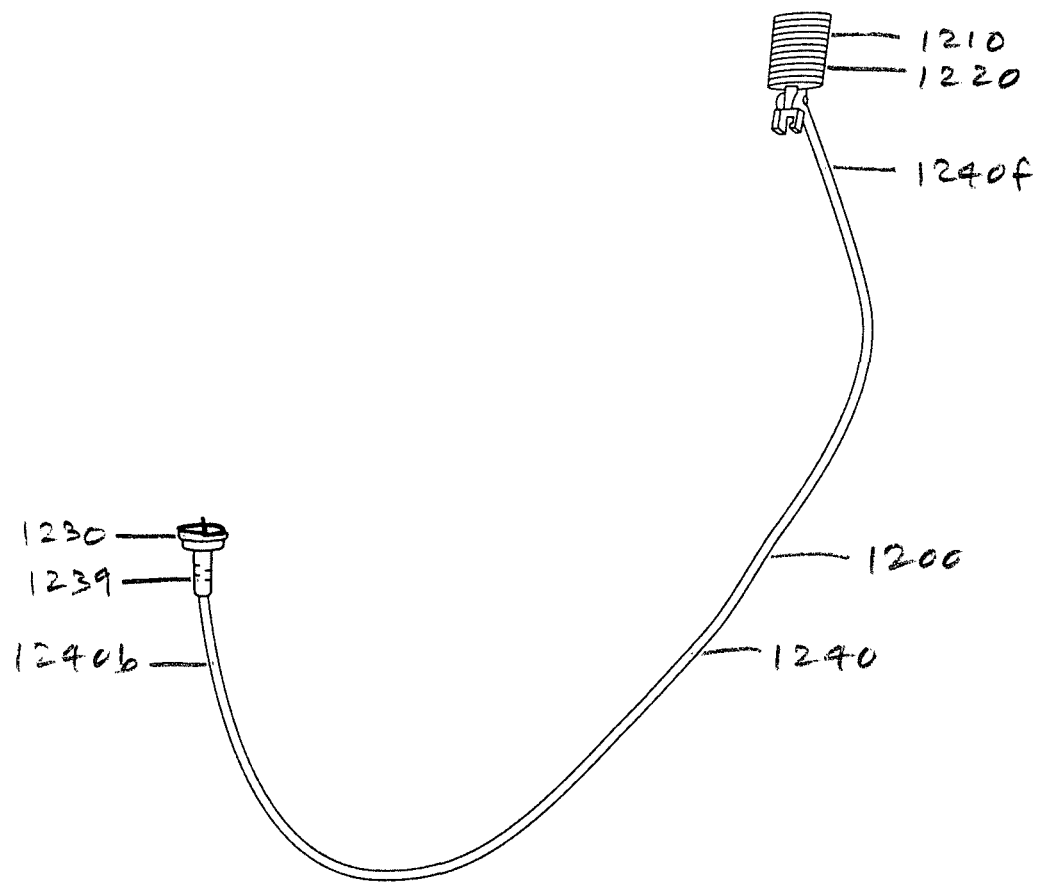
FIG. 3A shows one embodiment of a light assembly 1200.
Figure 3B:
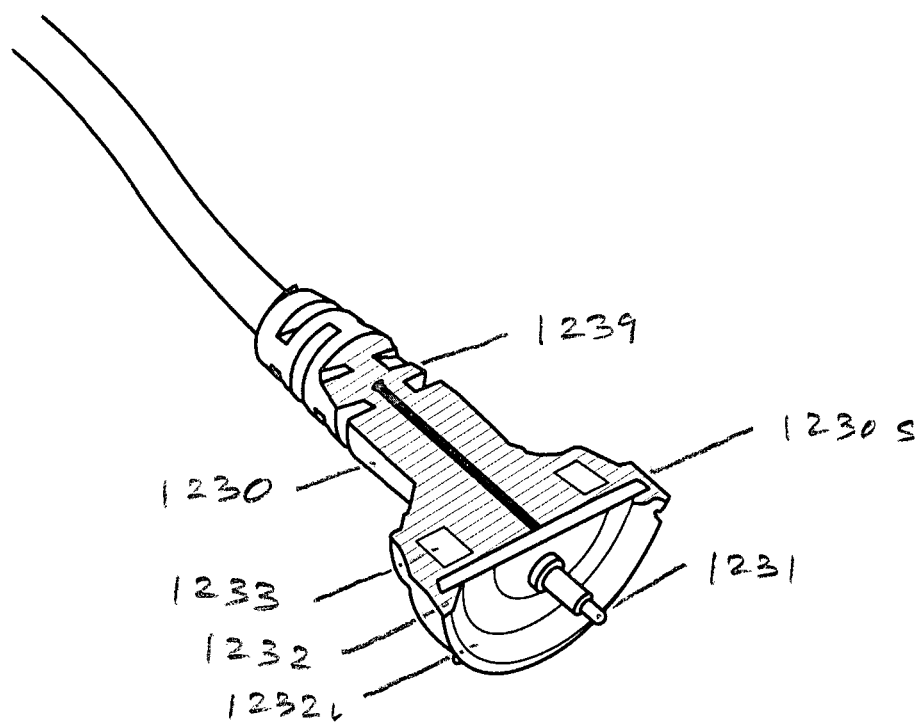
FIGS. 3B-3C show cross-sectional views of one embodiment of a light connector 1230.
Figure 3C:
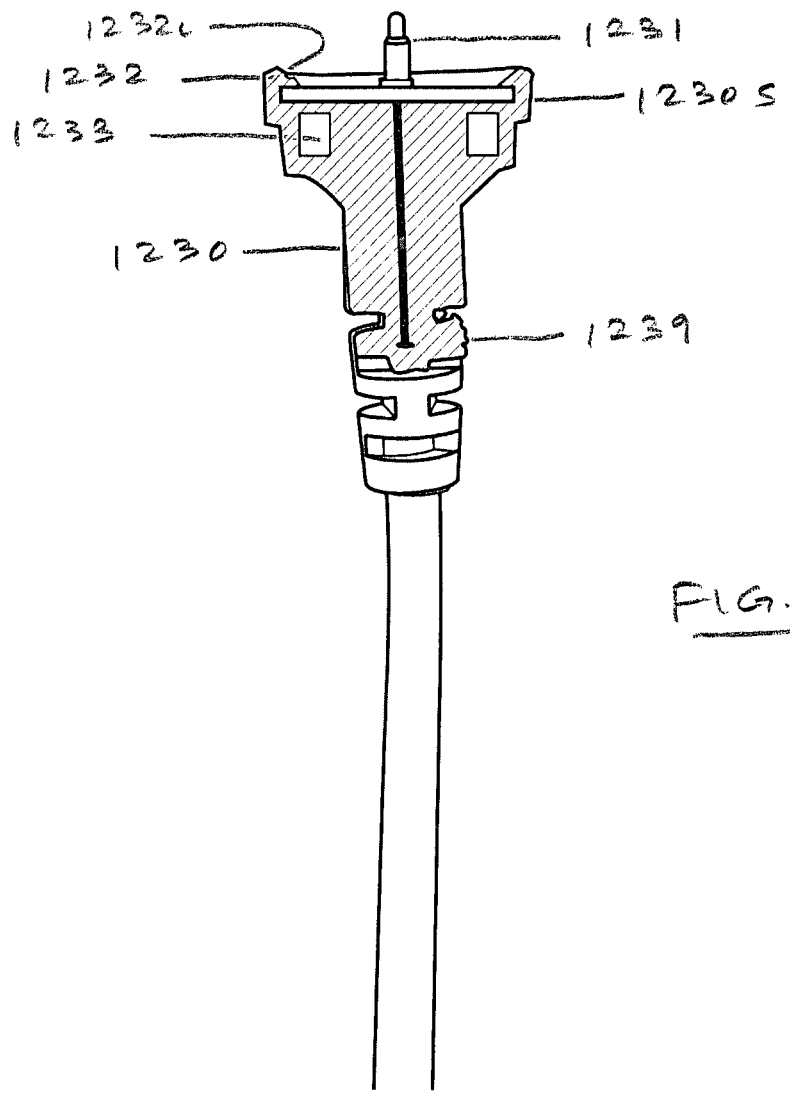

FIG. 3A shows one embodiment of a light assembly 1200. FIGS. 3B-3C show cross-sectional views of one embodiment of a light connector 1230.

Light assembly 1200 may include a light housing 1210. Light housing 1210 may be configured to be coupled to eyewear E, such as the bridge or the temple of eyewear E.

Light assembly 1200 may include a light source 1220. Light source 1220 may be coupled to light housing 1210. Light source 1220 may include one or more of an LED, an incandescent bulb, and any other suitable light source. Light source 1220 may produce one or more of visible light, UV light, IR light, and any other suitable wavelengths.

Light assembly 1200 may include a light connector 1230. Light connector 1230 may be capable of being electrically coupled to battery connector 1130. Light assembly 1200 may be capable of receiving power from battery assembly 1100 when light connector 1230 is electrically coupled to battery connector 1130.

Light connector 1230 may include a side surface 1230s. Side surface 1230s of light connector 1230 may have at least a portion that is substantially flat.

Light connector 1230 may have a diameter and/or width of approximately ⅛ inch or more.

Light connector 1230 may include one or more light contacts 1231. Light contacts 1231 may be capable of being electrically coupled to battery contacts 1131. Light contacts 1231 may include one or more of pins, contact pads, and any other suitable contact. Light contacts 1231 may include one or more pogo pins.

Light connector 1230 may include a lip 1232. Lip 1232 may at least partially surround light contacts 1231. Lip 1232 may be circular, octagonal, hexagonal, square, or any other suitable shape.

Light connector 1230 may be capable of being fittingly coupled to battery connector 1130. Lip 1232 of light connector 1230 and alignment feature 1132 of battery connector 1130 may align and/or center light connector 1230 with battery connector 1130. Lip 1232 may include an inner surface 1232i that is angled or beveled to align and/or center light connector 1230 with battery connector 1130. Lip 1232 of light connector 1230 may be capable of fitting and/or cooperating with alignment feature 1132 of battery connector 1130. Lip 1232 of light connector 1230 may be capable of fitting into and/or around alignment feature 1132 of battery connector 1130. Light connector 1230 may have a clearance fit with battery connector 1130.

When light connector 1230 is fittingly coupled to battery connector 1130, light connector 1230 is electrically coupled to battery connector 1130. When light connector 1230 is fittingly coupled to battery connector 1130, light contacts 1231 are electrically coupled to battery contacts 1131.

Light connector 1230 may include an attachment element 1233. Attachment element 1233 of light connector 1230 may be magnetically attracted to attachment element 1133 of battery connector. Attachment element 1233 may be at least partially made of a magnetic material such as neodymium, a ferromagnetic material such as iron, or other suitable material. Attachment element 1233 may be shaped like a ring, or any other suitable shape.

Light connector 1230 may be capable of being magnetically coupled to battery connector 1130. Attachment element 1233 of light connector 1230 may be capable of being magnetically coupled to attachment element 1133 of battery connector 1130.

Light connector 1230 may become magnetically coupled to battery connector 1130 when light connector 1230 is brought close to battery connector 1130. Attachment element 1233 of light connector 1230 may be urged toward attachment element 1133 of battery connector 1130 when light connector 1230 is brought close to battery connector 1130. Light connector 1230 may become magnetically coupled to battery connector 1130 when light connector 1230 is brought approximately 1 inch or less to battery connector 1130.

Light connector 1230 may be magnetically coupled to battery connector 1130 whether or not light connector 1230 is electrically coupled and/or fittingly coupled to battery connector 1130. When light connector 1230 is not electrically coupled or fittingly coupled to battery connector 1130, light connector 1230 may remain magnetically coupled to battery connector 1130, such as on side surface 1230s of light connector 1230.

When light connector 1230 is magnetically coupled to battery connector 1130, and light connector 1230 is electrically coupled and/or fittingly coupled to battery connector 1130, attachment element 1233 of light connector 1230 and attachment element 1133 of battery connector 1130 may bias light contacts 1231 against battery contacts 1131.

Attachment element 1233 of light connector 1230 may have a size similar to attachment element 1133 of battery connector 1130. Attachment element 1233 of light connector 1230 may have approximately the same diameter and/or width as attachment element 1133 of battery connector 1130. Attachment element 1233 of light connector 1230 and attachment element 1133 of battery connector 1130 may help to align and/or center light connector 1230 with battery connector 1130.

Light connector 1230 may include a strain relief 1239. Strain relief 1239 may have a height of approximately 0.25 inches or more.

Light assembly 1200 may include a wire 1240. Wire 1240 may include a front portion 1240f coupled to light housing 1210 and/or light source 1220. Wire 1240 may include a back portion 1240b coupled to light connector 1230. Back portion 1240b may be coupled to a center of light connector 1230, or any other suitable portion of light connector 1230. Wire 1240 may electrically couple light source 1220 to light connector 1230. Wire 1240 may carry power and/or a control signal.

Wire 1240 may be configured to be coupled to eyewear E, such as to the temple of eyewear E. Wire 1240 may be coupled to eyewear E at an attachment point 1240a. Attachment point 1240a may be adjusted along wire 1240 and/or on eyewear E. Wire 1240 may be coupled to eyewear E with an attachment 1241, such as a clip or a loop.

Light connector 1230 may be configured to be electrically coupled and/or fittingly coupled to battery connector 1130 when eyewear E is worn on the face of a user. Light connector 1230 may be configured to be not electrically coupled and not fittingly coupled to battery connector 1130 when eyewear E is not worn on the face of a user.

Wire 1240 may have an actual length, which may be the length of wire 1240 between light source 1220 and light connector 1230. Wire 1240 may have an effective length, which may be the length of wire 1240 between attachment point 1240a and light connector 1230. The effective length of wire 1240 may be adjusted by changing attachment point 1240a. The effective length of wire 1240 may be equal to the actual length if there is no attachment point 1240a.

The effective length of wire 1240 may be configured to cause and/or allow light connector 1230 to be electrically coupled and/or fittingly coupled to battery connector 1130 when eyewear E is worn on the face of a user. The effective length of wire 1240 may be long enough to cause and/or allow light connector 1230 to be electrically coupled and/or fittingly coupled to battery connector 1130 when eyewear E is worn on the face of a user.

The effective length of wire 1240 may be configured depending on a distance between attachment point 1240a and battery connector 1130 when eyewear E is worn on the face of a user. The effective length of wire 1240 may be configured depending on the size of the head of a user.

The effective length of wire 1240 may be configured to not allow light connector 1230 to be electrically coupled and/or fittingly coupled to battery connector 1130 when eyewear E is not worn on the face of a user. The effective length of wire 1240 may be short enough to not allow light connector 1230 to be electrically coupled and/or fittingly coupled to battery connector 1130 when eyewear E is not worn on the face of a user.

The effective length of wire 1240 may be configured depending on a distance between attachment point 1240a and battery connector 1130 when eyewear E is not worn on a the face of a user, such as when eyewear E is rested on the upper torso or the chest of a user. The effective length of wire 1240 may be configured depending on where eyewear E is rested on a user, which may depend on a length of eyewear retainer R, which may be adjustable.

The effective length of wire 1240 may be configured to cause and/or allow light connector 1230 to be magnetically coupled to battery connector 1130 when eyewear E is worn on the face of a user. The effective length of wire 1240 may be long enough to cause and/or allow light connector 1230 to be magnetically coupled to battery connector 1130 when eyewear E is worn on the face of a user. The effective length of wire 1240 may be configured to allow light connector 1230 to remain magnetically coupled to battery connector 1130, such as on side surface 1230s of light connector 1230, when eyewear E is not worn on the face of a user.

Wire 1240 may have an actual length of approximately 10 inches to approximately 30 inches, or approximately 12 inches to approximately 24 inches. Wire 1240 may have an effective length of approximately 10 inches to approximately 30 inches, or approximately 12 inches to approximately 24 inches. Wire 1240 may have a diameter of approximately 28 AWG to approximately 16 AWG. Wire 1240 may include stranded and/or solid wire.

Figure 4A:
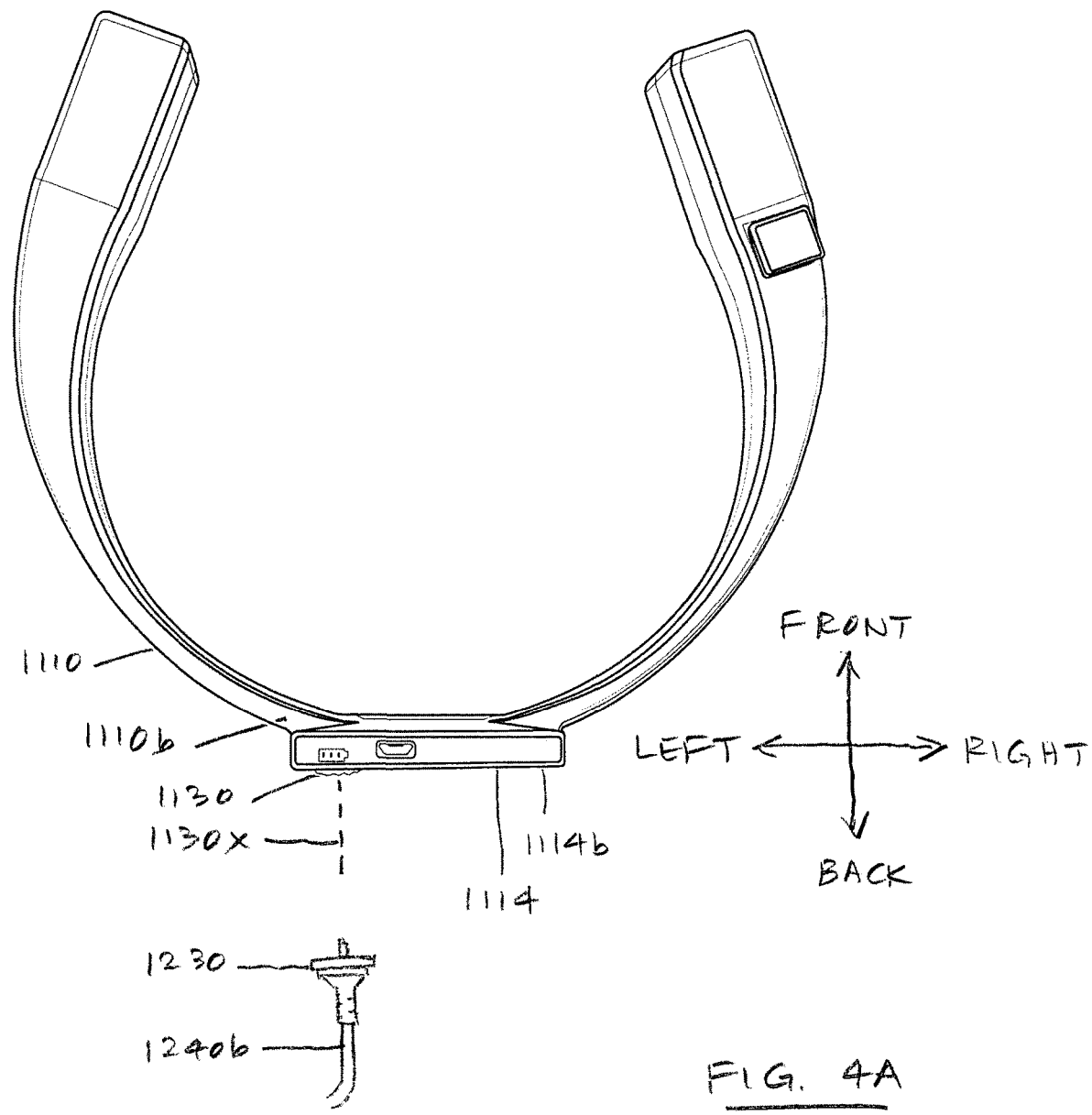
FIG. 4A shows one embodiment of an orientation of battery connector 1130.

FIG. 4A shows one embodiment of an orientation of battery connector 1130. Battery connector 1130 may be coupled to a back surface 1110b of battery housing 1110. Battery connector 1130 may be coupled to a back surface 1114b of pod 1114. Battery connector 1130 may face in the back direction, or up to approximately 45 degrees from the back direction. Alternatively, battery connector 1130 may face up, down, or any direction perpendicular to the left direction or the right direction, or up to approximately 45 degrees from any direction perpendicular to the left direction or the right direction.

Longitudinal axis 1130x of battery connector 1130 may point in the back direction, or up to approximately 45 degrees from the back direction. Alternatively, longitudinal axis 1130x of battery connector 1130 may point up, down, or any direction perpendicular to the left direction or the right direction, or up to approximately 45 degrees from any direction perpendicular to the left direction or the right direction.

When light connector 1230 is electrically coupled and/or fittingly coupled to battery connector 1130, strain relief 1239 and/or back portion 1240*b* of wire 1240 may extend from light connector 1230 in the back direction, or up to approximately 45 degrees from the back direction. Alternatively, strain relief 1239 and/or back portion 1240*b* of wire 1240 may extend up, down, or any direction perpendicular to the left direction or the right direction, or up to approximately 45 degrees from any direction perpendicular to the left direction or the right direction.

Figure 4B:
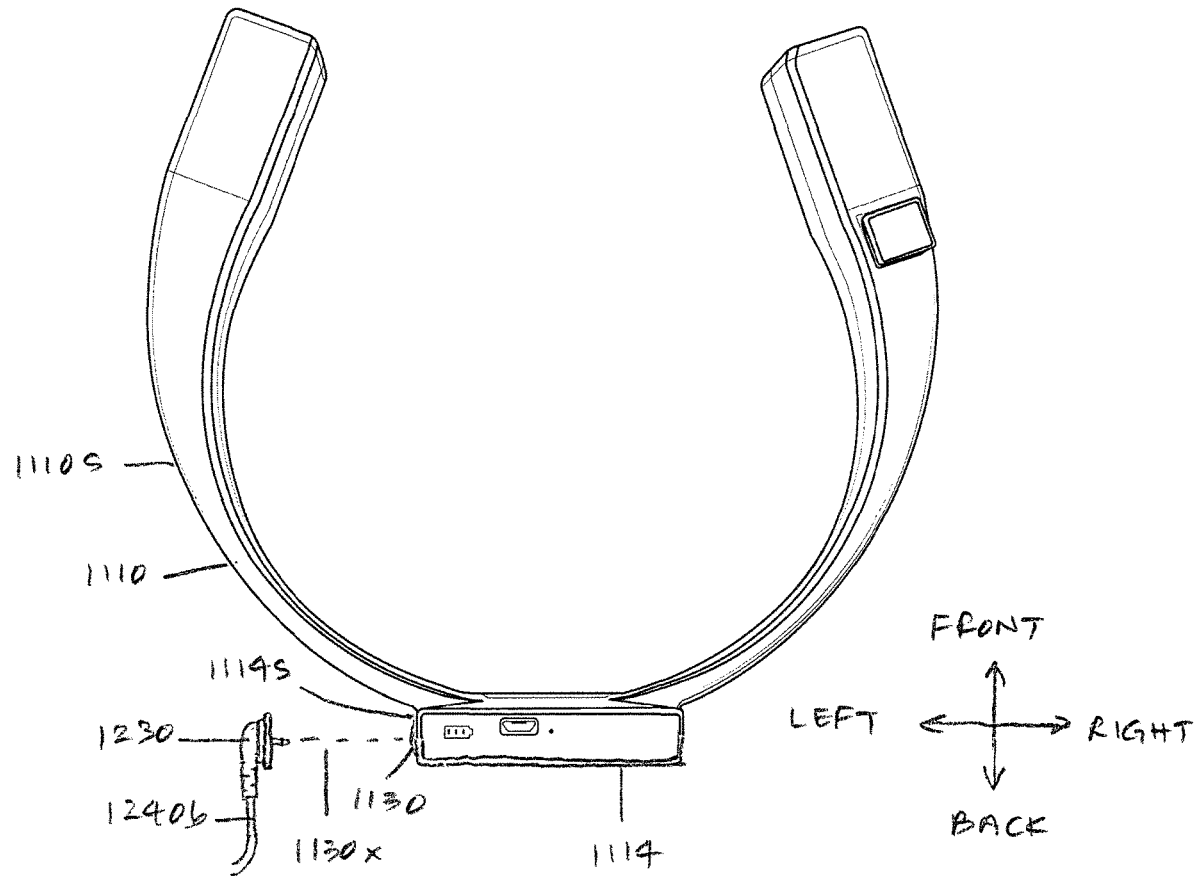
FIG. 4B shows another embodiment of an orientation of battery connector 1130.

FIG. 4B shows another embodiment of an orientation of battery connector 1130. Battery connector 1130 may be coupled to a side surface 1110*s* of battery housing 1110. Battery connector 1130 may be coupled to a side surface 1114*s* of pod 1114. Battery connector 1130 may face the left direction or the right direction, or up to approximately 45 degrees from the left direction or the right direction.

Longitudinal axis 1130*x* of battery connector 1130 may point in the left direction or the right direction, or up to approximately 45 degrees from the left direction or the right direction.

When light connector 1230 is electrically coupled and/or fittingly coupled to battery connector 1130, strain relief 1239 and/or back portion 1240*b* of wire 1240 may extend from light connector 1230 in the back direction, or up to approximately 45 degrees from the back direction. Alternatively, strain relief 1239 and/or back portion 1240*b* of wire 1240 may extend up, down, or any direction perpendicular to the left direction or the right direction, or up to approximately 45 degrees from any direction perpendicular to the left direction or the right direction.

Illumination device 1000 may include a hinge coupling 1300. Hinge coupling 1300 may be coupled to light connector 1230 and battery connector 1130. Hinge coupling 1300 may hingedly couple light connector 1230 to battery connector 1130. Hinge coupling 1300 may be configured to keep light connector 1230 hingedly coupled to battery connector 1130 whether or not light connector 1230 is electrically coupled and/or fittingly coupled to battery connector 1130.

Hinge coupling 1300 may have a closed configuration and an open configuration. In the closed configuration, light connector 1230 may be electrically coupled and/or fittingly coupled to battery connector 1130. In the open configuration, light connector 1230 may be in any position where light connector 1230 is not electrically coupled or fittingly coupled to battery connector 1130.

Hinge coupling 1300 may be biased toward the closed configuration, and only be in the open configuration when held or maintained in the open configuration. Alternatively, hinge coupling 1300 may be stable in both the closed configuration and the open configuration.

Figure 5A:
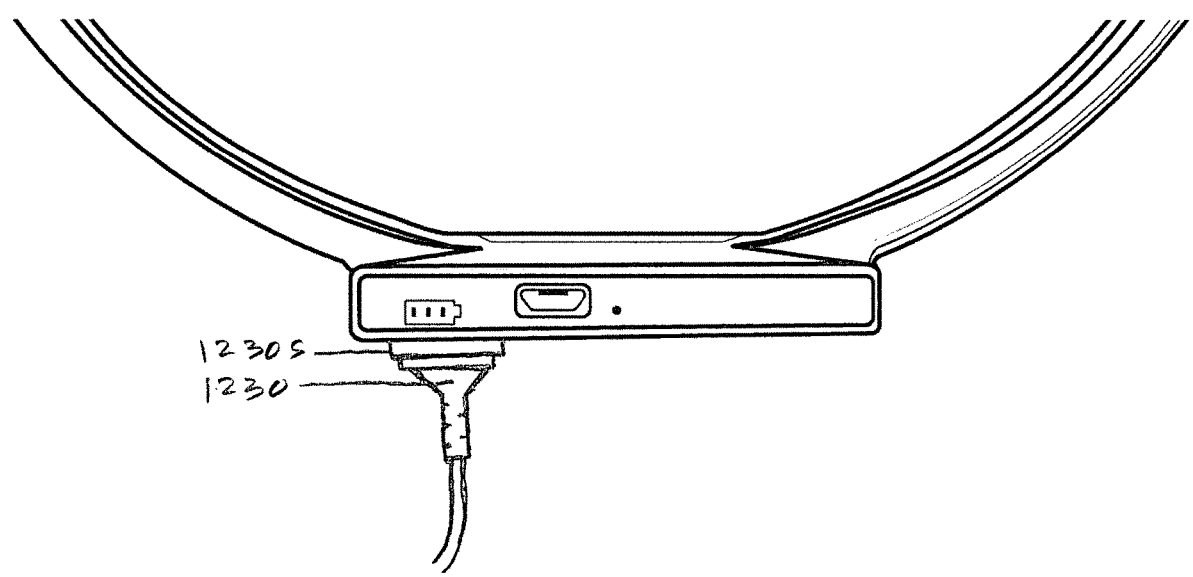
FIGS. 5A-5B show one embodiment of a hinge coupling 1300.
Figure 5B:
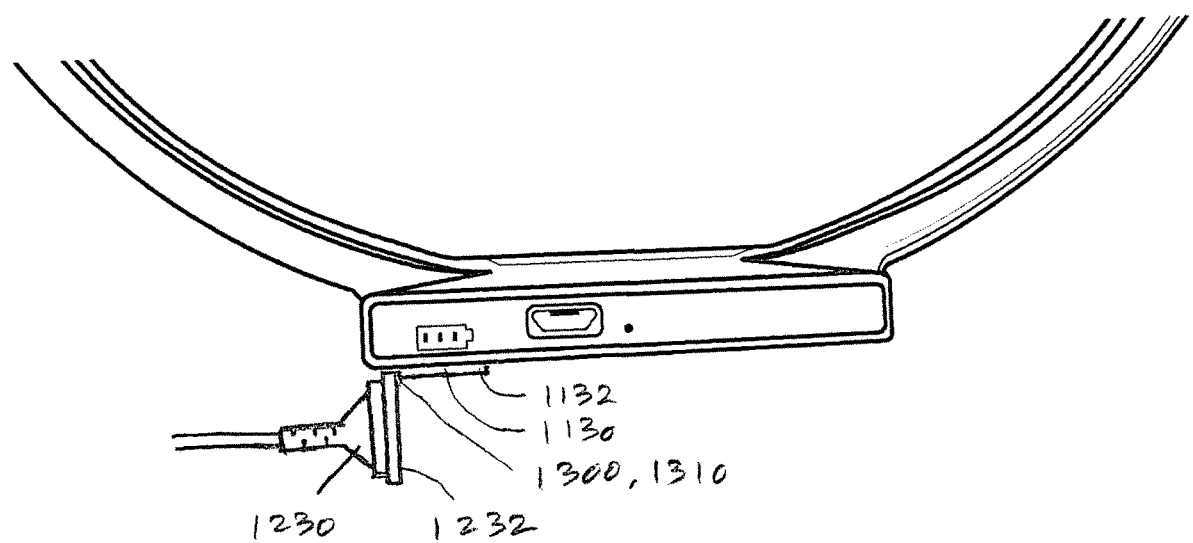

FIGS. 5A-5B shows one embodiment of a hinge coupling 1300. Hinge coupling 1300 may include a magnetic hinge 1310. Magnetic hinge 1310 may include attachment element 1233 of light connector 1230 and attachment element 1133 of battery connector 1130. Magnetic hinge 1310 may include lip 1232 of light connector 1230 and alignment feature 1132 of battery connector 1130.

FIG. 5A shows magnetic hinge 1310 in a closed configuration. Light connector 1230 may be electrically coupled and/or fittingly coupled to battery connector 1130.

FIG. 5B shows magnetic hinge 1310 in an open configuration. Light connector 1230 is not electrically coupled or fittingly coupled to battery connector 1130. Side surface 1230*s* of light connector 1230 may rest on or against battery connector 1130. Edge of lip 1232 may rest against alignment feature 1132.

Light connector 1230 may be magnetically coupled to battery connector 1130 when magnetic hinge 1310 is in both the closed configuration and the open configuration. Attachment element 1233 of light connector 1230 may be magnetically coupled to attachment element 1133 of battery connector 1130 when magnetic hinge 1310 is in both the closed configuration and the open configuration.

Lip 1232 of light connector 1230 may cooperate with alignment feature 1132 of battery connector 1130 to open magnetic hinge 1310. Lip 1232 of light connector 1230 may press against alignment feature 1132 of battery connector 1130 to open magnetic hinge 1310.

Magnetic hinge 1310 may be broken by separating light connector 1230 and battery connector 1130 to separate attachment element 1233 of light connector 1230 and attachment element 1133 of battery connector 1130. When magnetic hinge 1310 is broken, light connector 1230 may be not magnetically coupled to battery connector 1130.

Figure 5C:
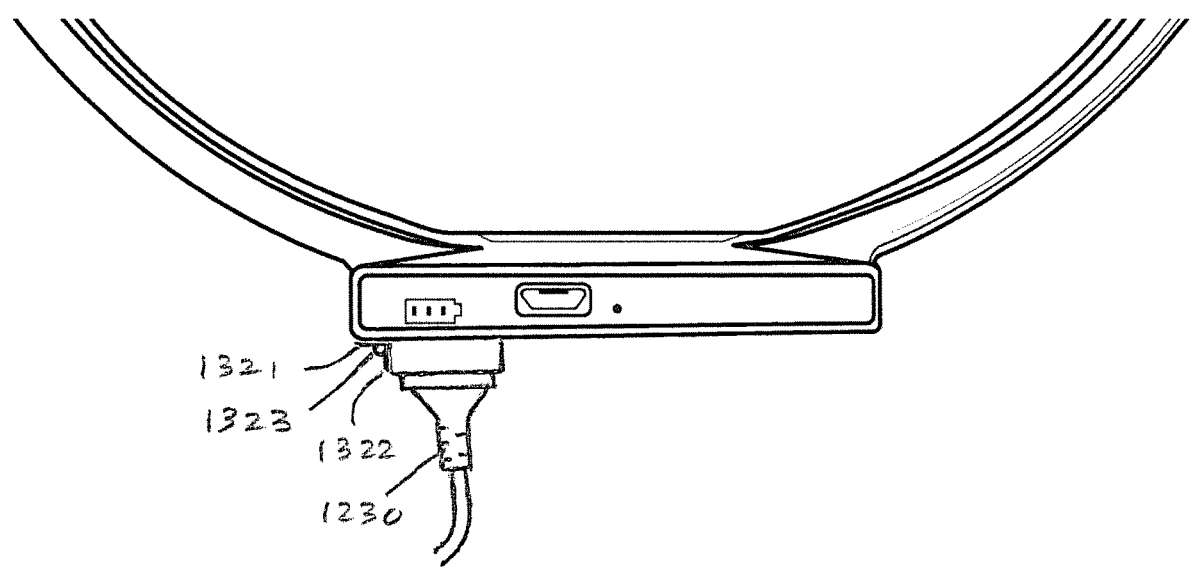
FIGS. 5C-5D show another embodiment of a hinge coupling 1300.
Figure 5D:
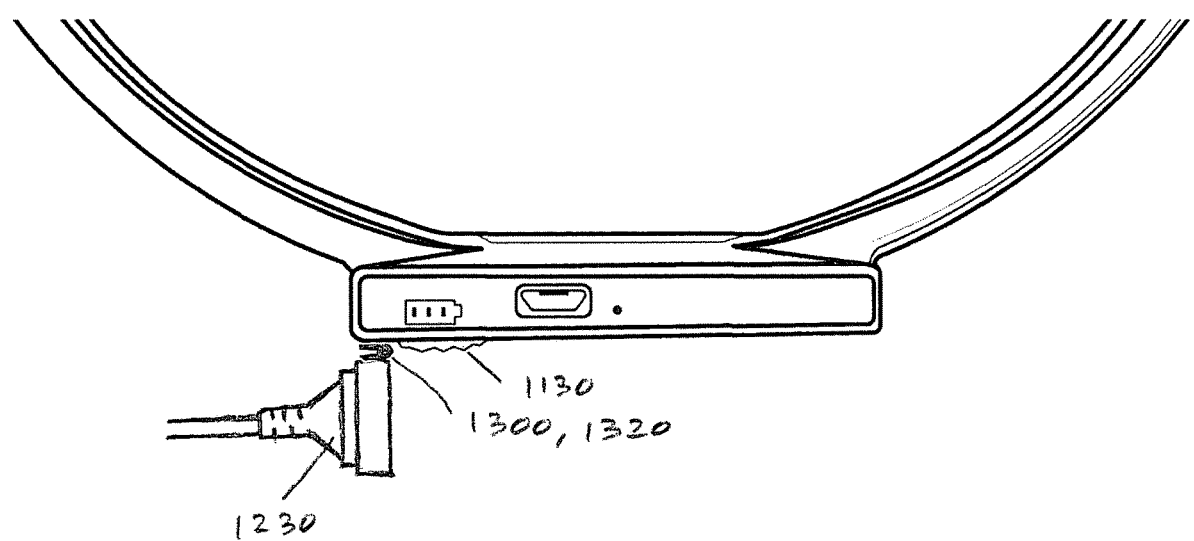

FIGS. 5C-5D show another embodiment of a hinge coupling 1300. Hinge coupling 1300 may include a mechanical hinge 1320. Mechanical hinge 1320 may include a first leaf 1321 and a second leaf 1322 coupled by a joint 1323. First leaf 1321 may be coupled to battery connector 1130. Second leaf 1322 may be coupled to light connector 1230. First leaf 1321 may be separably coupled to second leaf 1322. Mechanical hinge 1320 may be spring-loaded to be biased toward the closed configuration.

FIG. 5C shows mechanical hinge 1320 in a closed configuration. Light connector 1230 may be electrically coupled and/or fittingly coupled to battery connector 1130. Light connector 1230 may be magnetically coupled to battery connector 1130.

FIG. 5D shows mechanical hinge 1320 in an open configuration. Light connector 1230 is not electrically coupled or fittingly coupled to battery connector 1130. Light connector 1230 may be magnetically coupled to battery connector 1130 or not.

Mechanical hinge 1320 may be broken by disassembling joint 1323 to separate second leaf 1322 and first leaf 1321.

Figure 5E:
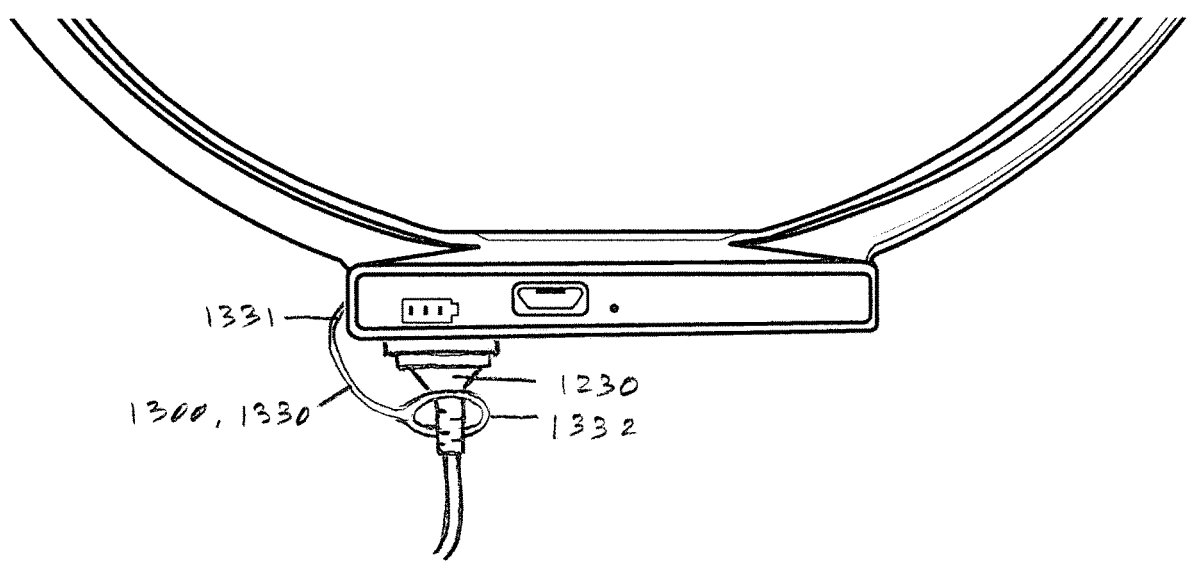
FIGS. 5E-5F show another embodiment of a hinge coupling 1300.
Figure 5F:
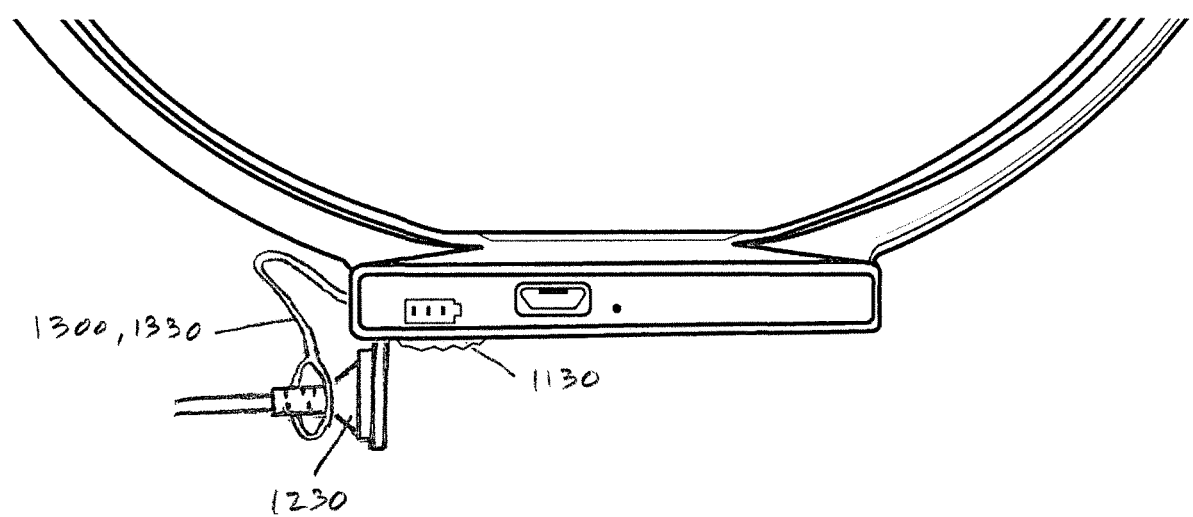

FIGS. 5E-5F show another embodiment of a hinge coupling 1300. Hinge coupling 1300 may include a tether coupling 1330. Tether coupling 1330 may include a first end portion 1331 and a second end portion 1332. First end portion 1331 may be coupled to battery connector 1130. Second end portion 1332 may be coupled to light connector 1230.

FIG. 5E shows tether coupling 1330 in a closed configuration. Light connector 1230 may be electrically coupled and/or fittingly coupled to battery connector 1130. Light connector 1230 may be magnetically coupled to battery connector 1130.

FIG. 5F shows tether coupling 1330 in an open configuration. Light connector 1230 is not electrically coupled and/or fittingly coupled to battery connector 1130. Light connector 1230 may be magnetically coupled to battery connector 1130 or not.

Figure 6A:
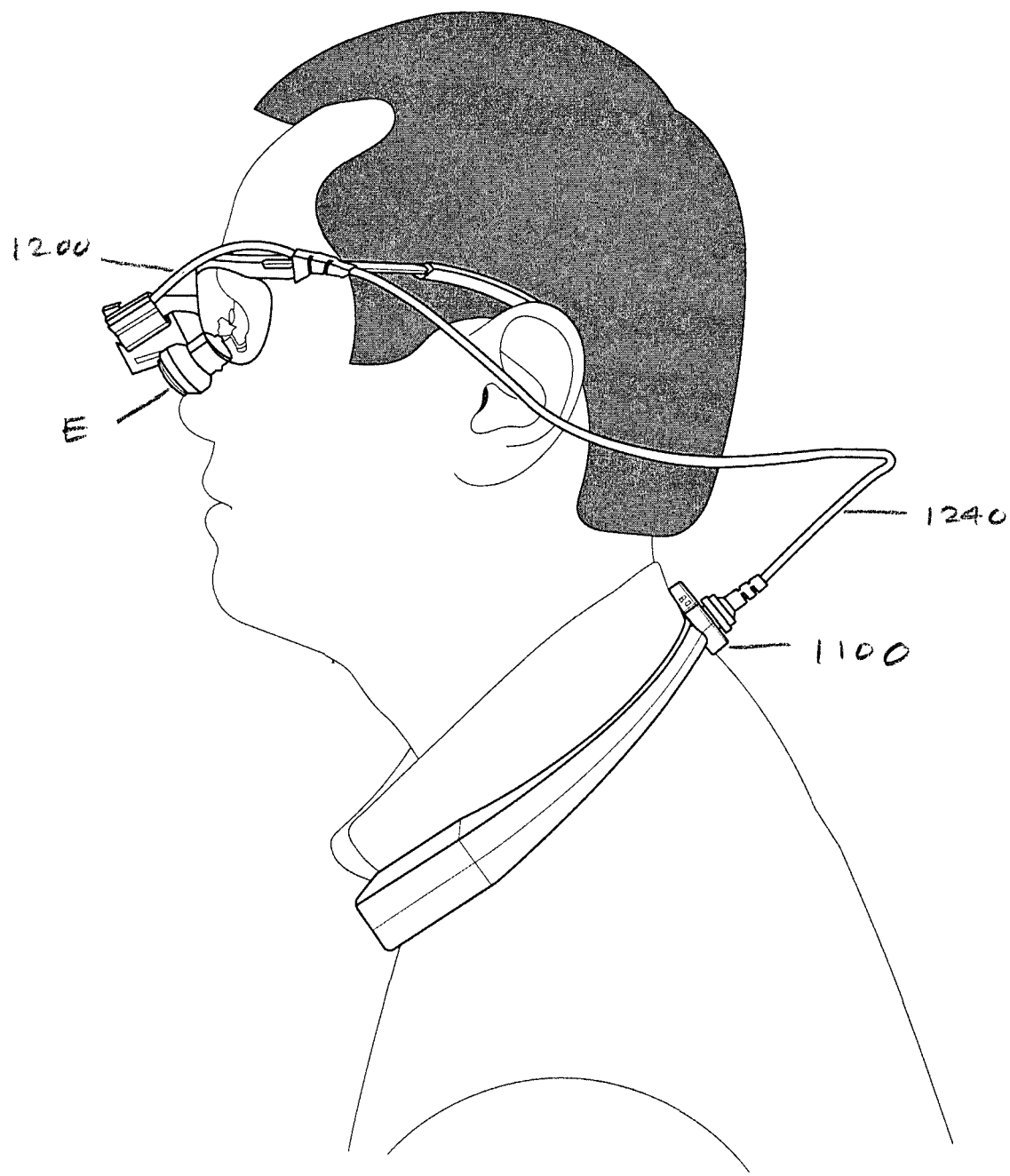
FIGS. 6A-6B and 7A-7B show one embodiment of a method of using illumination device 1000.
Figure 6B:
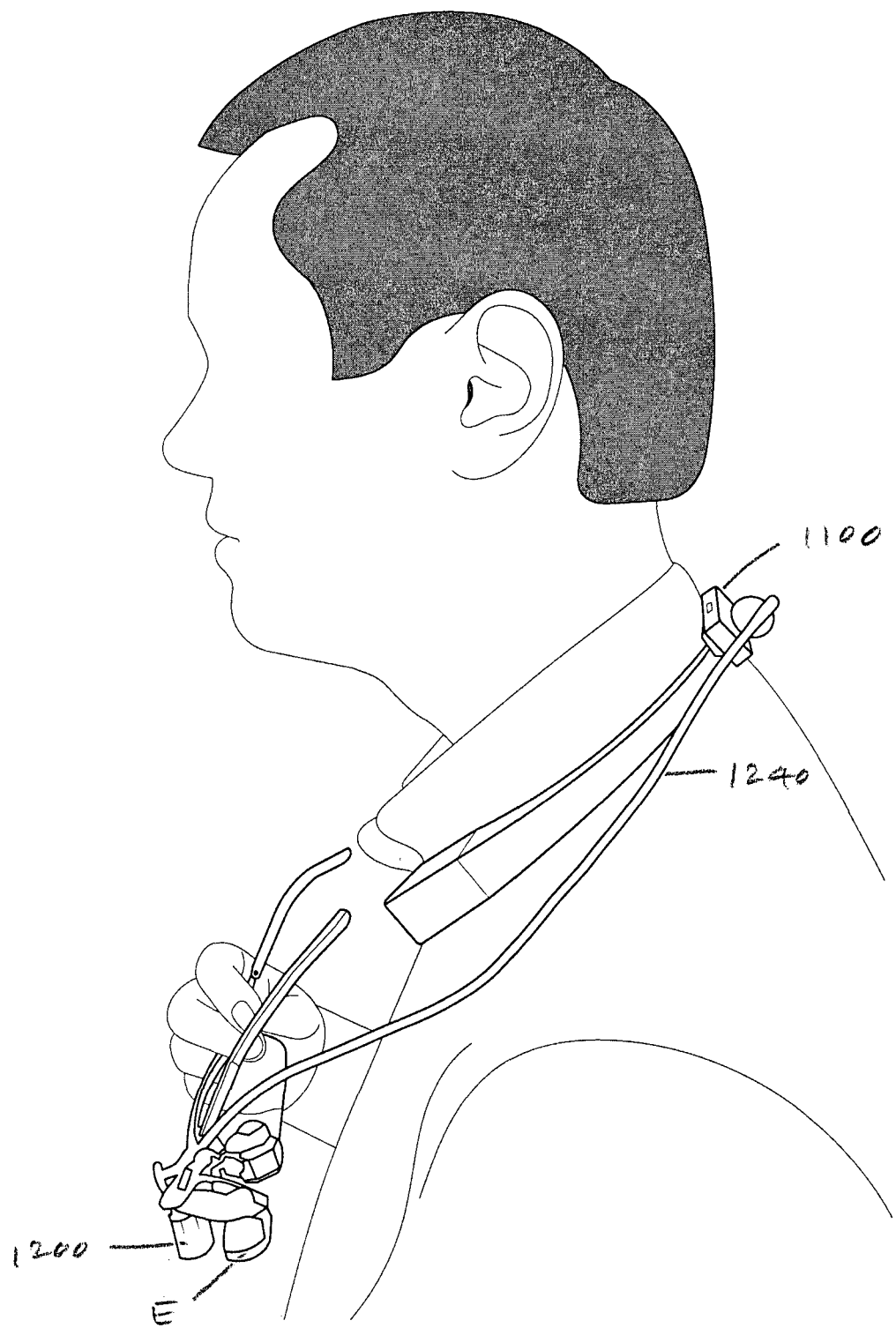
Figure 7A:
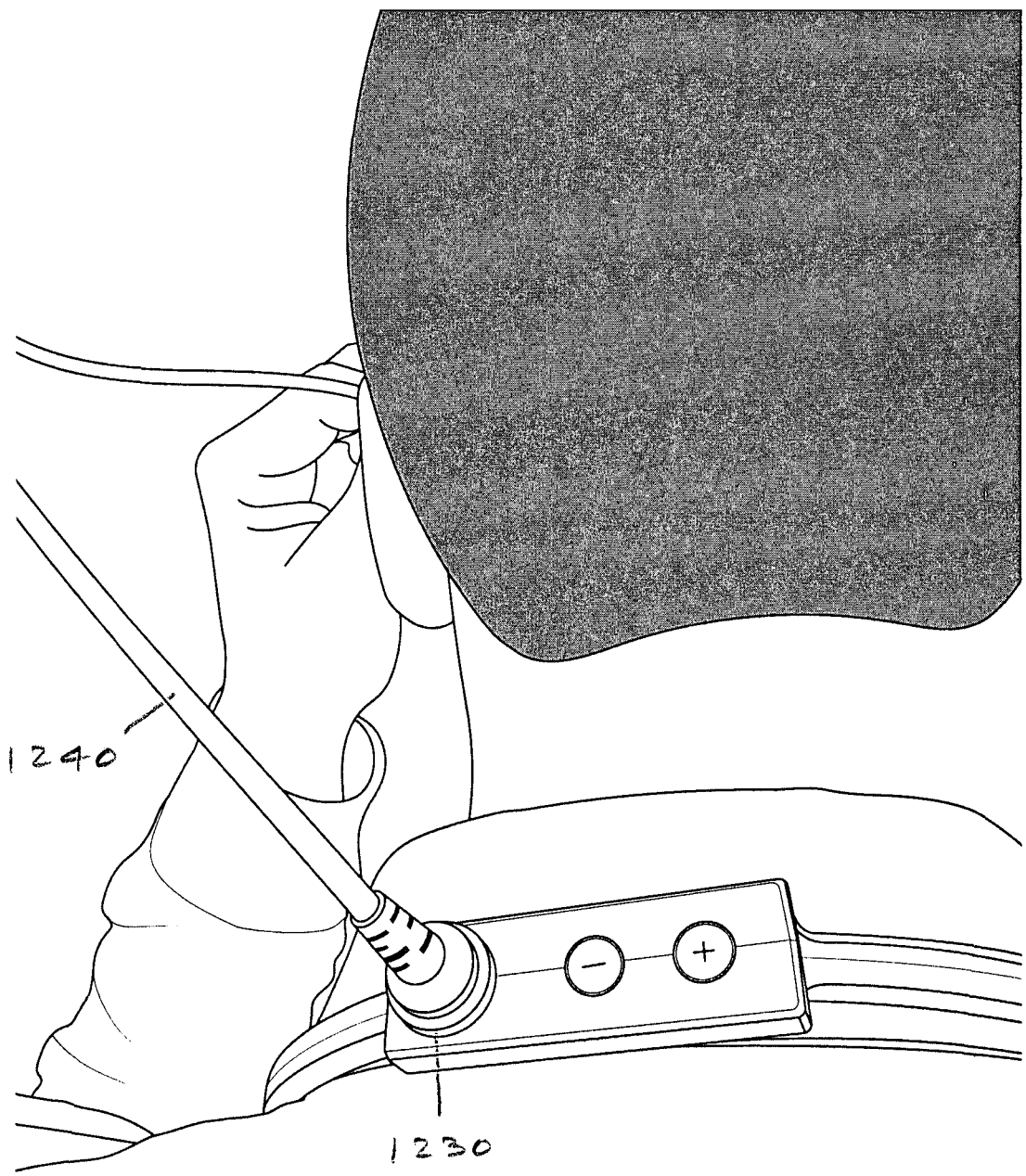
Figure 7B:
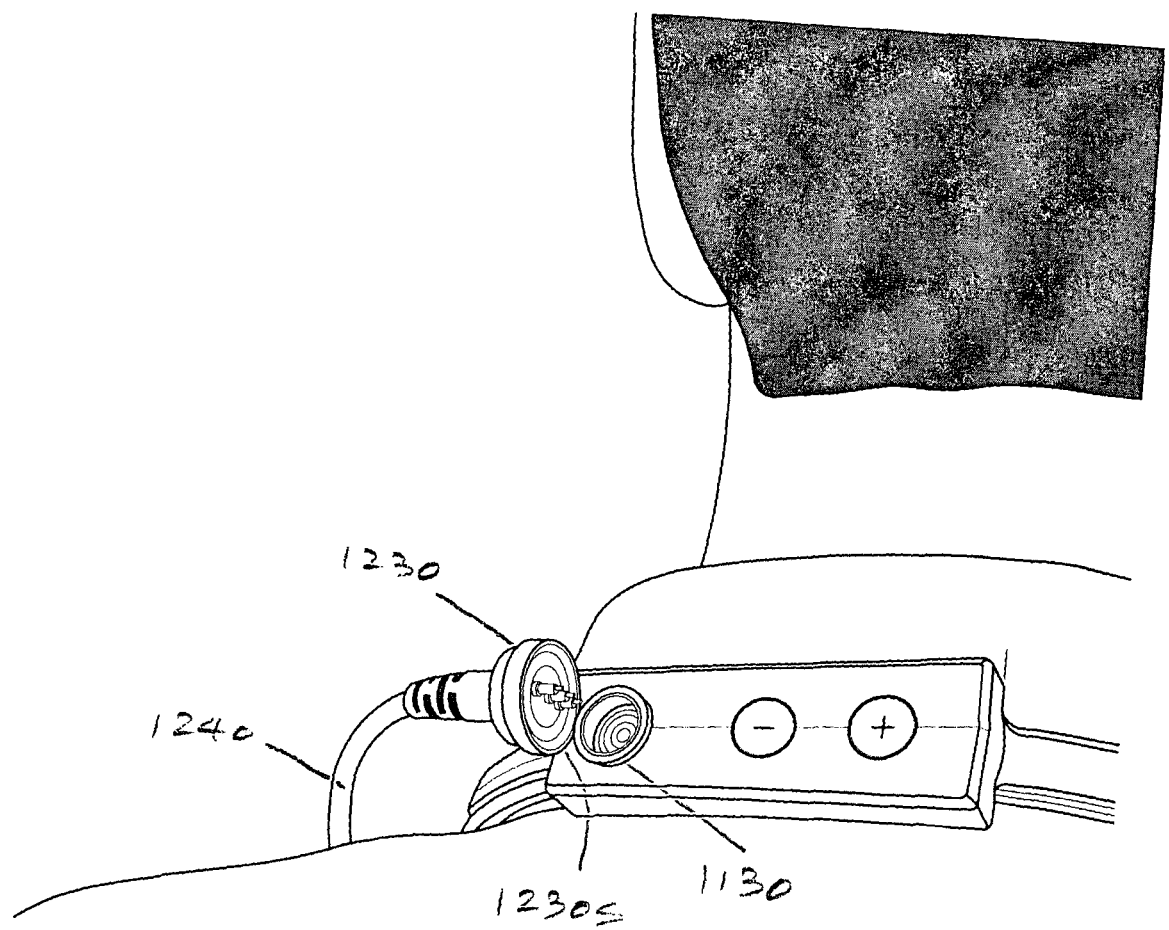

FIGS. 6A-6B and 7A-7B show one embodiment of a method of using illumination device 1000. FIGS. 6A-6B show a side view of the method. FIGS. 7A-7B show a rear view of the method.

Battery assembly 1100 is worn by a user. Light assembly 1200 is coupled to eyewear E. Hinge 1300 hingedly couples light connector 1230 to battery connector 1130.

FIGS. 6A and 7A show wearing eyewear E on the face to cause and/or allow light connector 1230 to be electrically coupled and/or fittingly coupled to battery connector 1130. Wearing eyewear E on the face gives enough of wire 1240 to cause and/or allow hinge coupling 1300 to close into the closed configuration, and causes and/or allows light connector 1230 to be electrically coupled and/or fittingly coupled to battery connector 1130. Attachment element 1233 of light connector 1230 and attachment element 1133 of battery connector 1130 urges light connector 1230 toward battery connector 1130, and light connector 1230 is magnetically coupled to battery connector 1130.

FIGS. 6B and 7B show removing eyewear E from the face to cause light connector 1230 to be not electrically coupled and/or not fittingly coupled to battery connector 1130. Removing eyewear E from the face pulls enough of wire 1240 to cause hinge coupling 1300 to open into the open configuration, and/or to cause light connector 1230 to be not electrically coupled and/or not fittingly coupled to battery connector 1130. Attachment element 1233 of light connector 1230 and attachment element 1133 of battery connector 1130 may keep light connector 1230 magnetically coupled to battery connector 1130. Side surface 1230s of light connector 1230 may rest on or against battery connector 1130.

Removing eyewear E from the face exerts a pull force on wire 1240, overcomes the magnetic attraction between light connector 1230 and battery connector 1130, and causes hinge coupling 1300 to open into the open configuration. The pull force needed on wire 1240 may be reduced by a moment arm created by the height of strain relief 1239 and/or the width of light connector 1230.

Figure 8A:
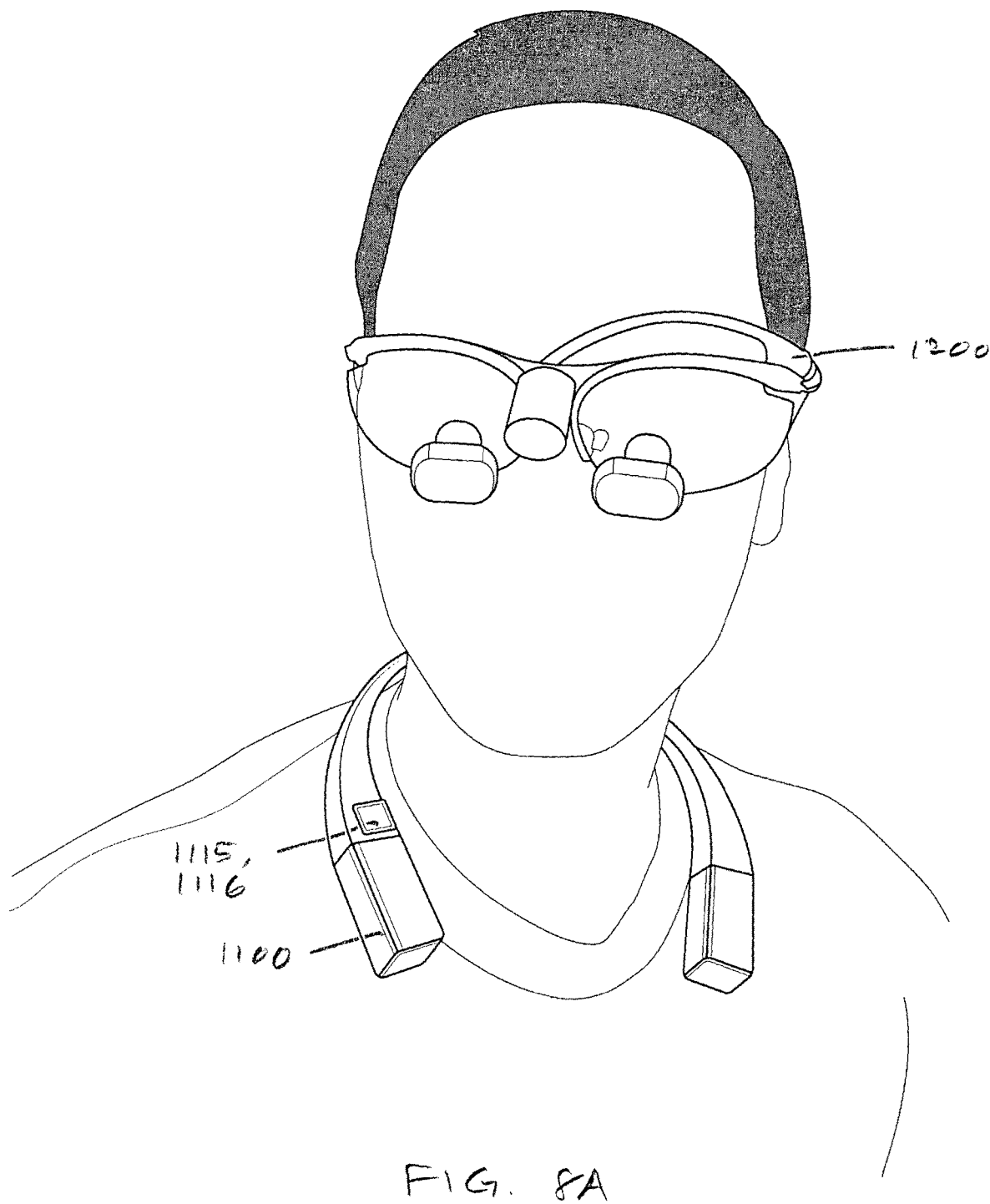
FIGS. 8A-8B show another embodiment of a method of using illumination device 1000.
Figure 8B:
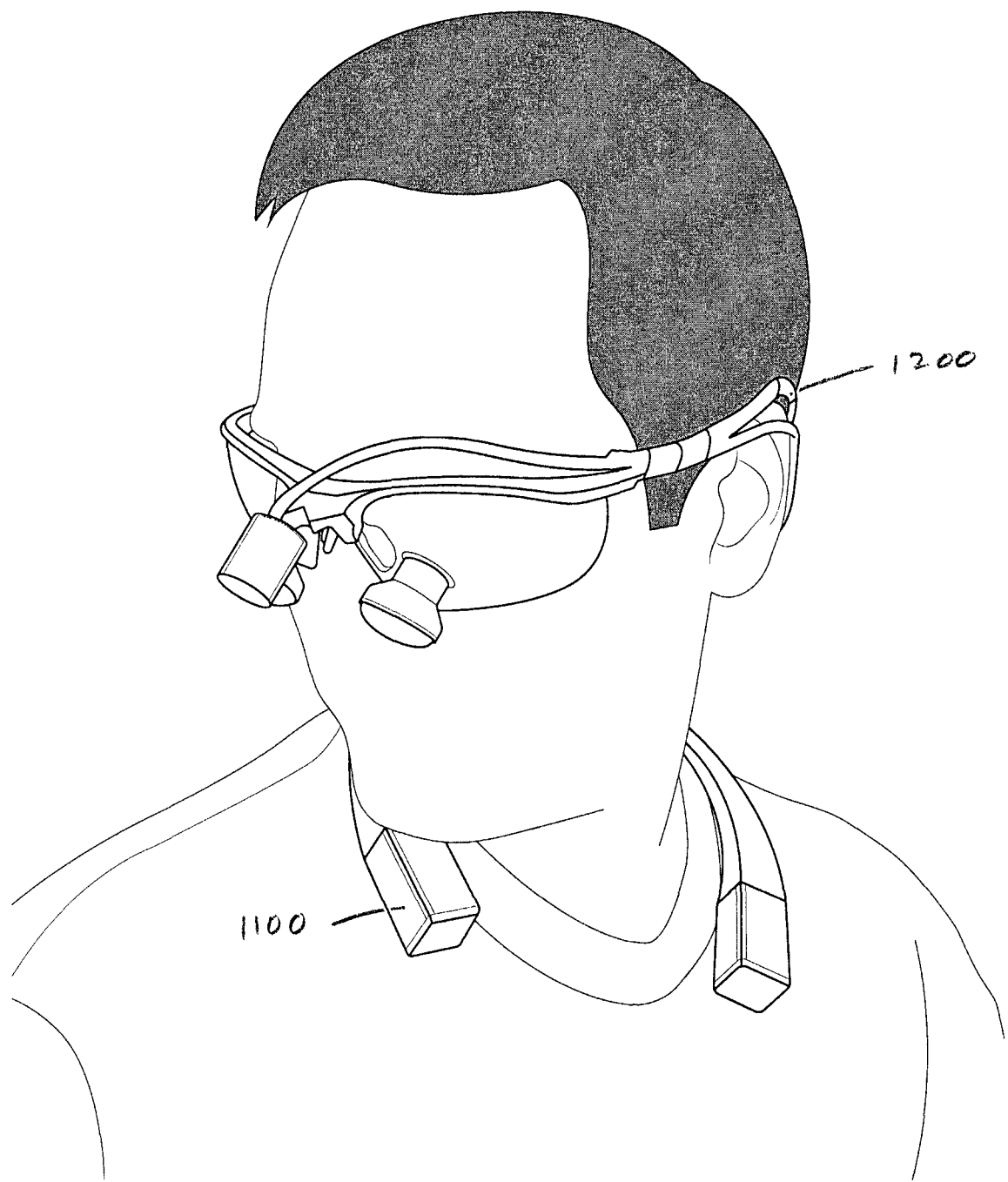

FIGS. 8A-8B show another embodiment of a method of using illumination device 1000.

FIG. 8A shows battery assembly 1100 worn by a user, light assembly 1200 coupled to eyewear E, and eyewear E worn on the face of the user.

FIG. 8B shows operating light control 1115 with a part of the face of a user. Operating light control 1115 may include pressing a power switch 1116 with the chin of the user to turn on light source 1220.

While the foregoing has been with reference to particular embodiments of the invention, it will be appreciated by those skilled in the art that changes in these embodiments may be made without departing from the principles and spirit of the invention.

What is claimed is:

1. An illumination device for use with eyewear, the eyewear capable of being worn on a face of a user, the illumination device comprising:
   a battery assembly having a battery housing and a battery connector, the battery connector having a first attachment element and a battery contact, the battery assembly configured to be worn by the user;
   a light assembly having a light source coupled by a wire to a light connector, the light connector having a second attachment element and a light contact, the light assembly configured to be coupled to the eyewear; and
   a magnetic hinge coupling the light connector to the battery connector, the magnetic hinge having a closed configuration in which the second attachment element is magnetically coupled to the first attachment element and the light contact is electrically coupled to the battery contact, the magnetic hinge having an open configuration in which the second attachment element is magnetically coupled to the first attachment element and the light contact is not electrically coupled to the battery contact and the light connector rests on a side surface of the light connector.

2. The illumination device of claim 1, wherein at least a portion of the battery housing is configured to be worn behind a neck of the user.

3. The illumination device of claim 2, wherein the battery connector is coupled to the portion of the battery housing configured to be worn behind the neck of the user.

4. The illumination device of claim 2, wherein the battery connector is coupled to a back surface of the battery housing.

5. The illumination device of claim 1, wherein the battery housing is U-shaped, the battery housing having a left portion and a right portion coupled to a center portion.

6. The illumination device of claim 5, wherein the center portion of the battery housing is configured to be worn behind a neck of the user, and the left portion and the right portion of the battery housing are configured to extend forward along the sides of the neck.

7. The illumination device of claim 5, wherein the battery connector is coupled to the center portion of the battery housing.

8. The illumination device of claim 5, wherein the battery connector is coupled to a back surface of the battery housing.

9. The illumination device of claim 1, wherein the battery connector includes an alignment feature and the light connector includes a lip, the alignment feature capable of fitting with the lip, the light connector capable of being fittingly coupled to the battery connector.

10. The illumination device of claim 1, wherein the wire is coupled to the eyewear at an attachment point by an attachment.

11. The illumination device of claim 10, wherein the wire has an effective length equal to the length of the wire between the attachment point and the light connector.

12. The illumination device of claim 11, wherein an effective length of the wire is configured to allow the light connector to be electrically coupled to the battery connector when the eyewear is worn on the face of the user, and the effective length of the wire is configured to not allow the light connector to be electrically coupled to the battery connector when the eyewear is not worn on the face of the user.

13. The illumination device of claim 12, wherein an effective length of the wire is configured to allow the light connector to be fittingly coupled to the battery connector when the eyewear is worn on the face of the user, and the effective length of the wire is configured to not allow the light connector to be fittingly coupled to the battery connector when the eyewear is not worn on the face of the user.

14. The illumination device of claim 13, wherein an effective length of the wire is configured to allow the light connector to be magnetically coupled to the battery connector when the eyewear is worn on the face of the user, and the effective length of the wire is configured to allow the light connector to remain magnetically coupled to the battery connector when the eyewear is not worn on the face of the user.

15. The illumination device of claim 1, wherein the battery connector faces in a back direction.

16. The illumination device of claim 1, wherein the wire extends from the light connector in a back direction when the light connector is electrically coupled to the battery connector.

17. A method of using an illumination device, the method comprising:
   providing the illumination device of claim 1;

wearing the eyewear on the face to give enough of the wire to cause and/or allow the hinge coupling to close into the closed configuration; and turning off the light source by removing the eyewear from the face to pull enough of the wire to cause the hinge coupling to open into the open configuration.

18. An illumination device for use with eyewear, the eyewear capable of being worn on a face of a user, the illumination device comprising:

a battery assembly having a battery housing and a battery connector, the battery connector having a first attachment element and a battery contact, the battery assembly configured to be worn by the user;

a light assembly having a light source coupled by a wire to a light connector, the light connector having a second attachment element and a light contact, the light assembly configured to be coupled to the eyewear; and a hinge coupling means hingedly coupling the light connector to the battery connector, the hinge coupling means having a closed configuration in which the second attachment element is magnetically coupled to the first attachment element and the light contact is electrically coupled to the battery contact, the hinge coupling means having an open configuration in which the second attachment element is magnetically coupled to the first attachment element and the light contact is not electrically coupled to the battery contact and the light connector rests on a side surface of the light connector.

* * * * *